(12) United States Patent
Schulz et al.

(10) Patent No.: US 12,030,838 B2
(45) Date of Patent: Jul. 9, 2024

(54) METHOD AND SYSTEM FOR THE PRODUCTION OF METHANOL

(71) Applicants: thyssenkrupp Industrial Solutions AG, Essen (DE); thyssenkrupp AG, Essen (DE)

(72) Inventors: Alexander Schulz, Frankfurt (DE); Steffen Schirrmeister, Muelheim an der Ruhr (DE)

(73) Assignees: thyssenkrupp Uhde GmbH, Dortmund (DE); thyssenkrupp AG, Essen (DE)

( * ) Notice: Subject to any disclaimer, the term of this patent is extended or adjusted under 35 U.S.C. 154(b) by 17 days.

(21) Appl. No.: 17/688,371

(22) Filed: Mar. 7, 2022

(65) Prior Publication Data
US 2022/0185751 A1 Jun. 16, 2022

Related U.S. Application Data

(62) Division of application No. 16/321,195, filed as application No. PCT/EP2017/068859 on Jul. 26, 2017, now abandoned.

(30) Foreign Application Priority Data

Jul. 26, 2016 (DE) .................. 10 2016 213 668.2

(51) Int. Cl.
*C07C 29/151* (2006.01)
*C07C 29/74* (2006.01)
(Continued)

(52) U.S. Cl.
CPC ...... *C07C 29/1512* (2013.01); *C07C 29/1518* (2013.01); *C07C 29/78* (2013.01);
(Continued)

(58) Field of Classification Search
None
See application file for complete search history.

(56) References Cited

U.S. PATENT DOCUMENTS

| 3,488,401 A | 1/1970 | Ames |
| 3,531,266 A | 9/1970 | Chernoff |
| (Continued) | | |

FOREIGN PATENT DOCUMENTS

| CN | 1157281 A | 8/1997 |
| CN | 102348667 A | 2/2012 |
| (Continued) | | |

OTHER PUBLICATIONS

Machine translation of WO 2014/173452 A1 (Oct. 2014). (Year: 2014).*

(Continued)

*Primary Examiner* — Jennifer A Leung
(74) *Attorney, Agent, or Firm* — thyssenkrupp North America, LLC

(57) ABSTRACT

A process for preparing methanol by a methanol synthesis reaction of carbon dioxide with hydrogen may involve a distillation step and a condensation step following the synthesis of a crude methanol. A volatile component and water may be separated off from a methanol-containing product stream, and a gas stream containing a volatile component that has been separated off may be discharged at least partially as offgas. At least part of the gas stream that has been separated off may be recirculated into the methanol synthesis reaction. A plant for preparing methanol can store or utilize electric power generated from renewable energy sources and provide facilities for discharging the offgas stream, which can be purified by catalytic after-combustion. Alternatively, the plant can be configured without discharge of an offgas substream, or the offgas streams are so small (Continued)

that they can be released without treatment into the environment at a suitable position.

18 Claims, 7 Drawing Sheets

(51) Int. Cl.
| | |
|---|---|
| *C07C 29/78* | (2006.01) |
| *C07C 29/80* | (2006.01) |
| *C07C 31/04* | (2006.01) |
| *C10J 1/00* | (2006.01) |
| *C10L 3/08* | (2006.01) |
| *C25B 1/04* | (2021.01) |
| *C25B 15/08* | (2006.01) |
| *F25J 3/02* | (2006.01) |

(52) U.S. Cl.
CPC ............. *C07C 29/80* (2013.01); *C10J 1/00* (2013.01); *C10L 3/08* (2013.01); *C25B 1/04* (2013.01); *C25B 15/08* (2013.01); *F25J 3/0223* (2013.01); *C10J 2300/1665* (2013.01); *C10L 2290/08* (2013.01); *C10L 2290/10* (2013.01); *C10L 2290/24* (2013.01); *C10L 2290/38* (2013.01); *C10L 2290/46* (2013.01); *C10L 2290/54* (2013.01); *C10L 2290/543* (2013.01); *Y02E 60/36* (2013.01); *Y02P 20/133* (2015.11)

(56) References Cited

U.S. PATENT DOCUMENTS

| | | | |
|---|---|---|---|
| 5,128,003 | A | 7/1992 | Murdoch |
| 5,364,887 | A * | 11/1994 | Konig ................ C07C 29/1516 518/728 |
| 5,770,630 | A | 6/1998 | Kowal |
| 2007/0244208 | A1 | 10/2007 | Shulenberger |
| 2007/0282021 | A1 | 12/2007 | Campbell |
| 2010/0205856 | A1 | 8/2010 | Kubic et al. |
| 2011/0203537 | A1 | 8/2011 | Prestel |
| 2011/0313064 | A1 | 12/2011 | Panza et al. |
| 2013/0237618 | A1 | 9/2013 | Matsushita et al. |
| 2013/0345325 | A1 | 12/2013 | Lecomte et al. |
| 2014/0316016 | A1 | 10/2014 | Jennings |
| 2014/0323600 | A1 | 10/2014 | Jennings |
| 2016/0237858 | A1 | 8/2016 | Bergins |

FOREIGN PATENT DOCUMENTS

| | | | | |
|---|---|---|---|---|
| CN | 104903281 A | | 9/2015 | |
| CN | 105622344 A | | 6/2016 | |
| DE | 3641774 A | * | 6/1988 | ........... C07C 29/154 |
| DE | 102009059310 A | | 6/2011 | |
| DE | 20 2010 012 734 U | | 1/2012 | |
| EP | 2228358 A1 | | 9/2010 | |
| EP | 2803654 A | | 11/2014 | |
| EP | 2 862 849 A | | 4/2015 | |
| WO | 2012028326 A | | 3/2012 | |
| WO | 2013029701 A | | 3/2013 | |
| WO | 2013053371 A | | 4/2013 | |
| WO | 2013144041 A1 | | 10/2013 | |
| WO | 2014/096226 A1 | | 6/2014 | |
| WO | 2014/173452 A | | 10/2014 | |
| WO | 2015/017875 A | | 2/2015 | |
| WO | 2015030578 A | | 3/2015 | |

OTHER PUBLICATIONS

English Translation of International Search Report issued in PCT/EP2017/068859, dated Sep. 18, 2017.

DPMAinformativ, Informationen über Patentdokumente des In- und Auslands (IPIA), German Patent Office, Version 2.8.1-5 (2015).[No English translation available. DPMAinformativ is a German-language publication by the German Patent and Trademark Office on specific topics in the filed of IP. This document is about patent documents from Germany and other countries, their kind codes and in which format they are published.].

Tanja Schaaf et al., Methanation of CO2-storage of renewable energy in a gas distribution system, Energy, Sustainability and Society—a SpringerOpen Journal, pp. 1-14 (2014).

\* cited by examiner

METHOD AND SYSTEM FOR THE PRODUCTION OF METHANOL

CROSS REFERENCE TO RELATED APPLICATIONS

This application is a divisional application of U.S. patent application Ser. No. 16/321,195, entitled "METHOD AND SYSTEM FOR THE PRODUCTION OF METHANOL" and filed Jan. 28, 2019, which is a U.S. National Stage Entry of International Patent Application Serial Number PCT/EP2017/068859, filed Jul. 26, 2017, which claims priority to German Patent Application No. DE 10 2016 213 668.2, filed Jul. 26, 2016, the entire contents of all of which are incorporated herein by reference.

FIELD

The present disclosure generally relates to processes for preparing methanol by reaction of carbon dioxide and hydrogen and to plants that can be used in connection with such processes.

BACKGROUND

In the move away from electric energy generated from fossil fuels to renewably generated energy, power peaks which can no longer be integrated into conventional electric grids occur. Various technologies for storing or otherwise utilizing power surpluses in times of surplus availability of renewable energies are summarized under the term "Power-to-X". One variant of this technology is named "Power-to-gas". Here, the surplus electric power from renewable energy sources is firstly converted by means of electrolysis of water into hydrogen. The hydrogen is subsequently reacted, for example, with carbon dioxide to form methane or methanol. The methane produced can, for example, be fed into the natural gas grid. As an alternative, the electrolytically generated hydrogen can also be reacted with nitrogen to form ammonia (this variant is also referred to as "Power-to-ammonia"). In this way, the energy can be stored chemically in the form of ammonia.

In comparison to the sometimes quite large electrolysis plants in the megawatts range, these Power-to-X plants are relatively small [for example in the order of from a few 1000 metric tons/year to several 10 000 metric tons/year (t/a)]. Economical and environmentally friendly disposal of purge gas and offgas streams from such plants, which are very largely operated in a stand-alone manner, is not realistically given by means of conventional flare systems. The term purge gases refers to gases which are present in a gas stream and are inert in respect of the desired reaction in a reaction of feed gases to form a product gas. Since the gases reacting with one another are usually circulated in such reactions, the inert gases and/or undesirable by-products may have to be removed as purge gases from the synthesis circuit so that they do not accumulate in the circuit.

DE 20 2010 012 734 U1 discloses a process in which hydrogen is produced by electrolysis of water in an electrolysis unit using electric energy produced from a renewable energy source and this hydrogen is subsequently reacted catalytically with carbon dioxide in a reactor unit in order to produce methanol or methane. The methane or methanol obtained here is burnt as hydrocarbon-containing energy carrier stream in a combustion chamber and the thermal energy of the flue gas formed in the combustion is then utilized to generate electric energy in a gas turbine process or a steam turbine process.

The document WO 2014/173452 A1 describes a process and a reactor plant for the synthesis of methanol with recycle gas and purge gas recirculation, where the methanol is produced in an exothermic reaction of carbon dioxide and hydrogen and the hydrogen used here is obtained by electrolysis of water. The product gas mixture from the methanol synthesis is here separated at the product outlet into a fraction comprising methanol-containing product, a recycle gas fraction and a purge gas fraction, with part of the purge gas fraction being recirculated to an entry stage and again conveyed through the reactor. The purge gas contains carbon dioxide, hydrogen and carbon monoxide. In one variant of the process, there is a purge stream which is discharged via a conduit into the atmosphere. Catalytic offgas purification is not provided for here.

US 2007/0282021 A1 discloses a process for preparing ethanol by reaction of carbon dioxide with hydrogen, in which not only ethanol but also other organic compounds such as methanol and higher alcohols as by-products are obtained. This known process is comparatively nonspecific since the desired product ethanol is obtained in a proportion of only 52%, while 26% of methanol and further alcohols having up to six carbon atoms are additionally formed. The product mixture can firstly be treated by stripping and then distilled in order to obtain a purified ethanol having a purity of 87%.

DE 20 2010 012 734 U1 describes a process for the catalytic production of methanol or methane from an electrolytically produced hydrogen stream and carbon dioxide. This process serves to equalize generation peaks in the generation of electric energy from renewable energy sources. The methanol produced in this process is subsequently burnt with the introduction of a stream of oxygen in a combustion chamber, so that it is not important to produce methanol having a high degree of purity since the methanol is not marketed as synthesis product. The treatment of the methanol-containing product stream is not described in more detail in this document. Catalytic offgas purification is not provided for in this known process.

Thus a need exists for an optimized process for preparing methanol by reaction of carbon dioxide and hydrogen in respect of the efficiency, the energy consumption, the offgas streams, and wastewater streams obtained and the product purity.

DETAILED DESCRIPTION

Figure 1:
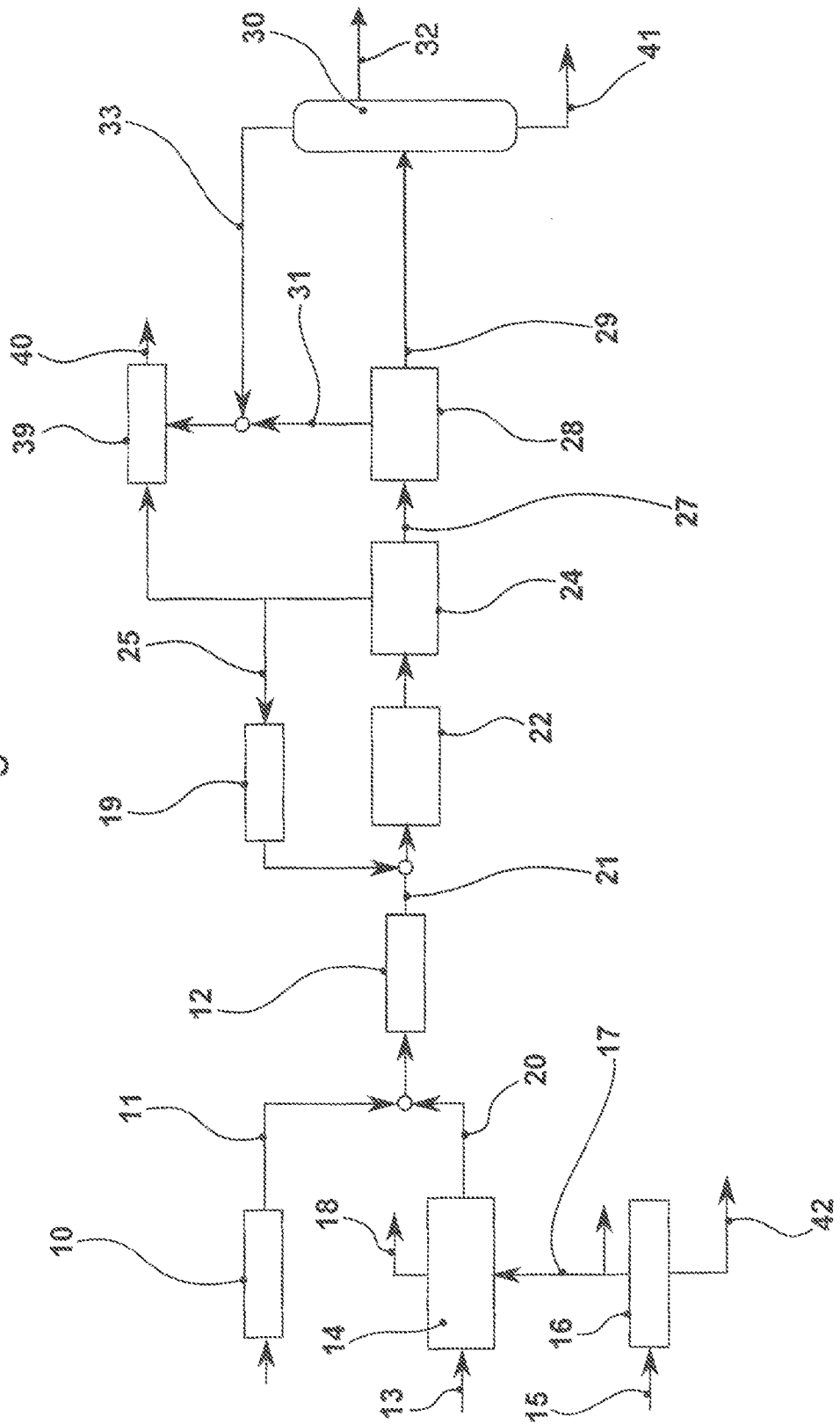
FIG. 1 is a schematic flow diagram of a first example plant for preparation of methanol with incineration of part of purge gases/offgases.

The present disclosure generally relates to processes for preparing methanol by reaction of carbon dioxide and hydrogen and also to plants that can be used in connection with such processes. In some examples, a product stream obtained in a methanol synthesis reaction may be fed to a high-pressure separator and/or a low-pressure separator in which a gas stream is separated off from a methanol-containing product stream.

The present invention primarily provides a process and a plant for preparing methanol. However, the process procedure described here and the plant conception are also suitable for the preparation of other alcohols, in particular lower alcohols such as ethanol.

According to the invention, the methanol-containing product stream obtained after the high-pressure separator and/or after the low-pressure separator are/is subsequently fed to at least one distillation step in which at least one component, in particular water, is separated off from the methanol-containing product stream.

In a preferred embodiment of the process, an at least one gas stream which has been separated off and contains volatile components is discharged in its entirety or only partly from the system as offgas and/or this gas stream or part of this gas stream which has been separated off is recirculated to the methanol synthesis reaction.

The process of the invention can, according to one of several possible alternative variants, be operated with such a plant configuration that an offgas stream is completely avoided or at least minimized. The offgas streams obtained as a result of the optimized configuration are so small in this variant of methanol production according to the invention that neither a flare nor offgas treatment are necessary in normal operation.

In one possible variant of the invention, catalytic offgas purification of an offgas stream and/or purge gas stream is preferably provided.

If such a catalytic offgas purification is provided, then this preferably comprises a catalytic after-combustion. This catalytic after-combustion is carried out with introduction of a supplementary combustion component.

If a catalytic after-combustion of the offgas stream is provided, the emission of, in particular, hydrocarbons into the environment can be produced. The offgas loaded with the pollutants is then passed through an apparatus in which at least one catalyst is present. The catalytic after-combustion operates according to the principle of heterogeneous catalysis. It is advantageous for this to be a process for offgas purification which can be carried out at a comparatively low reaction temperature. The hydrocarbons present in the offgas stream are generally oxidized to carbon dioxide and water. This oxidation can occur either directly or via intermediate stages.

As supplementary combustion component in the catalytic after-combustion, it is possible to use, for example, air or oxygen which is obtained in addition to $H_2$ in the electrolysis of water. Oxidation processes are assisted and/or accelerated by the addition of oxygen.

In the case of those variants in which no or only a minimal offgas stream is discharged from the system, volatile components separated off in the distillation or condensation can be recirculated back to the methanol synthesis reaction. An increase in the product yield and an improvement in the efficiency of the process overall are achieved in this way. In addition, these measures lead to avoidance of or a great reduction in environmental pollution.

The water separated off from the methanol- or methane-containing product stream in the distillation step can likewise be recirculated instead of being discharged as wastewater from the system; this is of particular interest in a preferred process variant in which the hydrogen used as starter material in the synthesis of methanol has previously been obtained from water by electrolysis. In this variant of the process of the invention, it is possible, for example, to use electric power previously obtained from, in particular, renewable energy sources for the electrolysis of water. The hydrogen produced here can then be reacted with carbon dioxide to form methanol (methanol synthesis). The product formed here is subsequently treated by suitable separation processes.

In principle, the process water can be sent directly to a sewage system in the processes according to the invention. However, disposal can be complicated in the case of decentralized plants. It is therefore advantageous for the process water to be able to be reused in the process according to the abovementioned process variant and not have to be disposed of. The utilization of the process water significantly reduces the freshwater requirement, for example by more than 30%.

In the variant with production of the hydrogen by electrolysis of water, treatment of the process water can be necessary, depending on the electrolysis technology used. This water treatment can, for example, comprise removal of methanol present in the water by means of a membrane process.

Salts can be removed from the freshwater introduced from the outside by, for example, ion exchange and/or reverse osmosis.

The carbon dioxide used as starter material in the methanol synthesis reaction can, for example, at least partly be made available cryogenically. In this case, the heat from the return stream of a cooling medium used in the process can be utilized for vaporization and heating of the carbon dioxide. This coupling of the cooling of a cooling medium from a closed cooling circuit with the vaporization and heating of $CO_2$ is an advantageous variant since no separate removal of heat is necessary for $CO_2$ vaporization and separate complicated cooling of the cooling medium can be dispensed with. As cooling medium, it is possible to use, for example, a glycol/water mixture. This can, for example, be precooled in a preceding air or water cooling step.

In one possible preferred variant of the process, a mixing and compression section which is supplied from the outside with carbon monoxide or hydrogen or a synthesis gas containing carbon oxides and hydrogen is provided upstream of the methanol synthesis reaction. In the methanol synthesis, the operating life of the catalyst is increased by the addition of carbon monoxide since deactivation of the catalyst proceeds more quickly in the case of pure carbon dioxide. If hydrogen is available at a site, this can be fed into the system and load can thus be taken off the electrolysis of water, so that the electric power requirement is reduced.

Further optimization of the process can be effected by combining the above-described system with, for example, a conventional synthesis gas production operation, for example by steam reforming, combined reforming or catalytic POX (autothermal reforming). The optimum position for the addition of external gases depends, inter alia, on the pressure level at which the gas is available.

If components which are inert in respect of the product synthesis and are not obtained in a mixture with the product and not in the water in the subsequent separation processes, for example nitrogen, get into the system via the addition of gas from the outside, a small offgas stream can be necessary in order to avoid accumulation of the inert components in the system. In the case of pure components, on the other hand, no offgas stream or a minimal offgas stream is envisaged.

In a basic version of the process of the invention, cryogenic carbon dioxide and electric power by means of which the hydrogen necessary for the synthesis is produced electrolytically from water can, for example, be provided as starting components. However, many alternative variants of the invention are possible when, for example, $CO_2$ is already present in gaseous form in a water treatment plant, a power station or the like or when, for example, $H_2$ is available via a pipeline or at the site of a chemical factory. In these cases, the vaporization and heating of the $CO_2$ or the reuse of the process water in the system can be dispensed with.

In embodiments of the process of the present invention, various further separation processes for the treatment and purification of the product stream can be provided in addition to the distillation. For example, a product stream obtained in the methanol synthesis reaction can firstly be fed to a low-pressure separator and a gas stream which has been separated off from the methanol-containing product stream in this low-pressure separator can subsequently be fed to the distillation step. Direct introduction of the gas phase from a low-pressure separator into a distillation apparatus has the advantages of minimizing the amount of offgas and increasing the total efficiency of the plant.

Volatile components separated off in the distillation step can be recirculated partly or in their entirety into a mixing and compression section located upstream of the methanol synthesis. This mixing and compression section can comprise one or more compressor stages connected in series. This is dependent on, inter alia, the reactor pressure. Many electrolyses of water operate at an elevated pressure of, for example, about 10 bara, so that $CO_2$ and $H_2$ can be mixed upstream of the compressor. In such a case, a recycled stream firstly has to be compressed in a first compressor stage before addition to $CO_2$ and $H_2$.

In other variants of the electrolysis of water, on the other hand, the hydrogen is obtained only at a small gauge pressure, for example in the region of a few 100 mbar. In this case, it is advantageous firstly to mix the recycled stream with $H_2$ and then compress it in a first compressor stage. $CO_2$ could then be added and the mixture then be compressed to the desired pressure.

In principle, it is possible to use a compressor having a plurality of stages or, as an alternative, two or more separate compressors.

In the methanol synthesis of the invention, water can be separated off at the bottom in the distillation step and the volatile components can be separated off at the top. The methanol obtained in this way can then, for example, be added to a spark-ignition fuel. If high-purity methanol is to be produced, it is advantageous to use two or more distillation columns.

In another preferred embodiment of the present invention, a product stream obtained in the methanol synthesis reaction is firstly fed to a high-pressure separator and a gas stream which has been separated off from a methanol-containing product stream in this high-pressure separator is partly recirculated as recycle gas to the methanol synthesis reaction and a further substream from the high-pressure separator is fed to the distillation step.

In a preferred further development of the abovementioned variant, it is possible, for example, for a gaseous product stream obtained in a methanol synthesis reaction firstly to be fed, after cooling, to a high-pressure separator in which a first gas stream is separated off from a liquid methanol-containing product stream and the methanol-containing product stream then to be fed, with a reduction in pressure, to a low-pressure separator in which a second gas stream is separated off from the methanol-containing product stream, with the first gas stream being at least partly recirculated as recycle gas to the methanol synthesis reaction, the second gas stream subsequently being fed to the distillation step and the remaining methanol-containing product stream likewise being fed to the distillation step.

The recirculation of the overhead product from the distillation step into a mixing and compression section advantageously results in a significant minimization of the amount of offgas and an increase in the overall efficiency of the plant.

Taking off a substream from the recycle gas to the distillation apparatus firstly enables a constant stream to be recirculated via a recycle compressor to the reactor. Secondly, the $H_2$ to $CO_2$ ratio can be set within particular limits by the division of the fluid stream. If this substream is omitted, it is advantageous to discharge part of the recycle stream (of the stream from the distillation apparatus to the mixing and compression section). At each of these two places, it is also possible to provide a small offtake stream (offgas stream).

A small offgas stream can occur when a catalyst having a poor selectivity is used, as a result of which there is increased formation of by-products, or when unfavorable operating parameters (for example high temperatures) are selected when deactivation of the catalyst has already progressed and by-products are thus formed to an increased extent.

If offgas streams to be purified, which are despite small amounts fed to the catalytic offgas purification, are obtained in the process of the invention, these can contain, for example, carbon monoxide and/or carbon dioxide and/or water and also residues of methanol, hydrogen and by-products such as methyl formate and dimethyl ether.

The synthesis of methanol by the process of the invention is preferably carried out at temperatures in the range from about 200° C. to about 300° C.

The present invention further provides a plant for preparing methanol by reaction of carbon dioxide with hydrogen, comprising at least one reactor unit for the synthesis of methanol and comprising at least one first separation apparatus which is located downstream of the reactor unit and has the function of separating off volatile and/or liquid constituents from a methanol-containing product stream, wherein the plant further comprises at least one further separation apparatus which is located downstream of the first separation apparatus and has the function of separating off volatile constituents by distillation or of separating off water by condensation, with at least one return conduit connected to the separation apparatus being provided for at least partial recirculation of a gas stream separated off in the separation apparatus to a region upstream of the reactor unit and/or at least one offgas conduit connected to the separation apparatus being provided for partial or complete discharge of an offgas stream from the plant.

The plant of the invention preferably further comprises an electrolysis apparatus for producing hydrogen from water and also means for feeding the hydrogen produced in the electrolysis to the reactor unit for the preparation of methanol. The electric energy coming, for example, from power peaks can be used for the electrolytic production of hydrogen from water in the electrolysis apparatus. Since hydrogen cannot easily be stored, it is advantageous to convert the hydrogen into another energy carrier, for which purpose it is preferably reacted with carbon dioxide to form methanol according to the invention. The methanol can be stored in suitable tanks and can be utilized as energy carrier at a given point in time or else be used as reactive component for producing further basic chemicals.

If offgas streams which have to be discharged from the system arise in one of the abovementioned process variants, the plant of the invention preferably further comprises at least one apparatus for catalytic offgas purification of an offgas stream and/or purge gas stream to be discharged from the plant, which apparatus is indirectly or directly in active communication with the reactor unit via the offgas conduit.

This plant preferably further comprises at least one compressor which is arranged between the electrolysis apparatus and the reactor unit and by means of which the feed gas stream can be brought to the entry pressure necessary for the reactor unit.

Furthermore, the plant of the invention preferably comprises, as first separation apparatus, at least one high-pressure separator which is located downstream of the reactor unit and has the function of separating gaseous constituents from a methanol-containing product stream. In the high-pressure separator, liquid components such as methanol and water can be separated off from volatile components by means of prior cooling and high pressure. As cooling medium, it is possible to use, for example, the cooling medium which has been cooled in the $CO_2$ vaporizer. Cooling by means of water or air is likewise possible in principle.

Furthermore, the plant of the invention preferably comprises, as separator apparatus, at least one low-pressure separator which is located downstream of the reactor unit, preferably located downstream of a high-pressure separator, and has the function of separating off liquid and/or gaseous constituents from a methanol-containing product stream. In the low-pressure separator, the fluid mixture is depressurized so as to produce a gas phase which can then, for example, be fed either in its entirety or only partly to the distillation apparatus. In the latter variant, a substream from the low-pressure separator can be discharged as offgas from the system, optionally after catalytic purification. However, such discharge of offgas can, as an alternative, also occur after the distillation apparatus which according to the invention is preferably used as further separation apparatus.

In order to introduce the components which have been separated off in the distillation apparatus back into the methanol synthesis, the plant of the invention preferably comprises at least one return conduit for recirculation of a gas stream which has been separated off in the distillation apparatus into a region upstream of the reactor unit.

If discharge of a substream as offgas from the process is provided for, this can also occur, for example, after the separation operation in the high-pressure separator, so that in this case the plant preferably comprises at least one gas conduit from the high-pressure separator to the apparatus for catalytic offgas purification. As an alternative, discharge of a substream as offgas after the separation operation in the low-pressure separator can also be provided for, so that at least one gas conduit from the low-pressure separator to the apparatus for catalytic offgas purification is then preferably provided. Otherwise, the discharge of a substream as offgas or purge gas occurs after the distillation, so that at least one gas conduit which leads from the distillation apparatus to the catalytic offgas purification is then preferably provided. As a result of recirculation of the components separated off in the distillation and the routing according to the invention of the gas streams from the separators, possible offgas streams are minimized to such an extent that offgas purification is not absolutely necessary. However, it is advantageous to ensure a suitable position for blowing-off into the surroundings.

In a preferred embodiment of the present invention, a recycle gas is recirculated from the high-pressure separator into the methanol synthesis. In this variant, at least one return conduit for gases extending from the high-pressure separator to the entry region of the reactor unit is provided, with the plant then preferably further comprising a compressor arranged in the flow path between the high-pressure separator and an entry region of the reactor unit, preferably in the return conduit.

In the abovementioned area, it is also possible to provide for a substream of the recycle gas to be separated off from the high-pressure separator and conveyed into the distillation apparatus. In this preferred variant, a branch conduit branching off from the return conduit extending from the high-pressure separator is provided for feeding at least one substream of the volatile constituents separated off in the high-pressure separator into the upper region of the distillation apparatus. This branch conduit can then in turn open into a conduit which serves for feeding volatile constituents separated off in the low-pressure separator into an upper region of the distillation apparatus. A further possible variant of the invention provides for the hydrogen to be stored in a hydrogen store which is preferably arranged downstream of one or more compressors and upstream of the reactor unit for the methanol synthesis. In this way, a failure of the power supply could be bridged for a certain period of time and the capacity of the plant could thus be adapted in a regulated manner and the plant could continue to be operated at part load. It is also possible to provide a separate compressor for the hydrogen store in order to store the hydrogen at high pressure and then introduce it back into the compressor section when required.

Some preferred operating conditions for the methanol synthesis according to the process of the invention are indicated below. The reaction in the methanol synthesis reactor is preferably carried out at a temperature in the range from 200° C. to 300° C., in particular from 210° C. to 280° C., and at a pressure of preferably from 30 to 100 bara (bar absolute), in particular at from 40 to 100 bara.

High temperatures can lead to increased deactivation of the catalyst and to increased formation of by-products.

The methanol synthesis can be controlled in a targeted manner and the formation of by-products minimized by means of the molar ratio of the two reactants hydrogen to carbon dioxide at the reactor inlet. The stoichiometric ratio for the synthesis of methanol from hydrogen and carbon dioxide is 3:1. However, a superstoichiometric ratio of $H_2$ to $CO_2$ at the reactor inlet in the range from 5 to 12 can preferably be selected in order to decrease the deactivation of the catalyst.

Any reactor type is in principle possible for the methanol synthesis reactor. For example, the reactor can be a water-cooled shell-and-tube reactor.

The catalysts known to a person skilled in the art for the reaction are in principle possible for the methanol synthesis according to the invention. There are no specific restrictions in respect of the catalyst for this reaction. Copper-based catalysts may be mentioned only by way of example.

In the following, reference is made firstly to FIG. 1. In the working example, this is, in particular, a "small-scale" plant for methanol production having a capacity in the order of, for example, up to several 10 000 t/a. An external source of carbon dioxide is provided; this carbon dioxide can, for example, be present cryogenically and is fed to a vaporizer 10 from where the $CO_2$ goes via a conduit 11 into the compressor 12. The second starter material for the preparation of methanol is hydrogen, which is obtained electrolytically from water. Electric power 13 obtained from renewable energy sources is preferably used to operate the electrolysis apparatus 14. The starter material for the electrolysis is water which is conveyed via a conduit 15 firstly optionally into a work-up apparatus 16 in which, for example, a reverse osmosis and/or an ion exchange is provided. From there, the treated water goes via the conduit 17 as starter material into the electrolysis apparatus 14. At this point, a substream of freshwater for a possible steam and condensate system and/or a closed cooling medium circuit can, for example, be branched off. The wastewater from the treatment apparatus can in the simplest case be discharged from the system via the wastewater conduit 42.

The electrolysis of water forms not only hydrogen but also oxygen which can be discharged via a conduit 18 from the electrolysis apparatus 14 and either be used as supplementary combustion component in the catalytic after-combustion of the purged gases/offgases or else is passed to another use outside the system. The hydrogen produced in the electrolysis is fed via the conduit to the compressor 12 to which the $CO_2$ is also fed via the conduit 11. From the compressor 12, the combined feed mixture of $CO_2$ and $H_2$ is then fed via the conduit 21 into the methanol synthesis reactor 22.

The methanol synthesis takes place in the methanol synthesis reactor 22 and the product stream leaving this reactor is fed via the conduit 23 to a high-pressure separator 24. From this, it is possible to provide a return conduit 25 to a compressor 19 in which a starter material-containing gas mixture which has been separated off from the product stream in the high-pressure separator 24 is compressed and, after compression, recirculated and fed back into the methanol synthesis reactor 22. In the present example, this methanol synthesis reactor 22 operates at an elevated temperature, for example in the order of from 200° C. to 300° C., and at an elevated pressure which can be, for example, in the range from about 30 bar to 100 bar. In addition, a catalyst is generally used for the methanol synthesis. The methanol-containing product stream leaving the methanol synthesis reactor 22 is fed into a high-pressure separator 24, leaves the latter via the conduit 27 and is then optionally fed to a low-pressure separator 28 in which further separation of gases from the methanol-containing product stream occurs.

Further purification of this crude methanol takes place in a distillation apparatus 30 which is connected via a conduit to the low-pressure separator 38 and in which volatile components are separated off and are discharged from the top of the distillation apparatus 30 via a conduit 33 and in the simplest case can optionally be discharged as offgas from the system. Furthermore, a second conduit 31 extending from the low-pressure separator 28 is provided; volatile components separated off there can likewise be introduced via this conduit into the offgas stream. These volatile components can, particularly when small amounts are obtained, be burnt by means of a flare 39 and the offgas can be discharged from the system via the conduit 40.

Apart from the volatile components, water can be separated off from the methanol at the bottom of the distillation apparatus 30 and the waste water can in the case of this simple plant be discharged from the system via the conduit 41. The methanol is then discharged from the system in a high purity via the conduit 32 and can, for example, be stored in tanks.

Part of the volatile components separated off in the high-pressure separator 24 is conveyed as recycle gas via the return conduit 25 to a further compressor 19 and then from there fed into the conduit 21 for starter materials, so that these components can be recirculated to the methanol synthesis reactor 22.

A second working example of a plant according to the invention for preparing methanol is described below with reference to FIG. 2. The structure is similar to the working example described above with the aid of FIG. 1, since this is also a relatively small plant (small-scale) in a basic configuration, but, as a difference from the example of FIG. 1, an offgas purification is provided. All plant components which correspond to the structure according to the figure are not explained again here. In this respect, reference is made to what has been said above. The difference from the example of FIG. 1 is that an apparatus 36 for catalytic offgas purification is provided instead of the flare 39.

The gas stream leaving the top of the distillation apparatus 30 is conveyed via the gas conduit 33 (see FIG. 1) to a catalytic after-combustion 36. The proportion of volatile components separated off in the high-pressure separator 24 is taken as purge gas stream from the circuit and fed via conduit 35 to the apparatus 36 for catalytic after-combustion. This can be fed together with oxygen, which is obtained as by-product in the electrolysis apparatus 14, via the conduit 18, so that, depending on the composition of the purge gases, the oxygen introduced as supplementary combustion component can serve to promote the combustion. The catalytic after-combustion occurs in the apparatus 36, so that a purified offgas stream which leaves the plant via the discharge conduit 37 is produced.

A third working example of the present invention is explained below with reference to FIG. 3. This variant differs from the two above-described working examples firstly in that the formation of offgas has been minimized. The fluid stream of the volatile components separated off in the distillation apparatus 30 is here recirculated as recycle stream via the return conduit 34 into a region located upstream of a first compressor or a first compressor stage 12 and upstream of the methanol synthesis reactor 22. Unlike the above-described variants, a first compressor (compressor stage) 12 to which firstly the hydrogen from the electrolysis 14 and also this recycle stream is fed is provided here. The mixture leaving the first compressor 12 is then fed together with the carbon dioxide supplied from the vaporizer 10 via the conduit 11 to a further compressor or a further compressor stage 26, since multiple compression is necessary in order to bring the feed gases to the pressure envisaged for the methanol synthesis. From the outlet of this further compressor 26, the feed stream then goes into the methanol synthesis reactor 22 which is additionally supplied with the recycle gas recirculated from the high-pressure separator 24 via the return conduit 25 after it has been compressed in the compressor 19.

Furthermore, the water obtained at the bottom in the distillation is in this variant not discharged from the system but instead circulated via the return conduit as process water back into the water electrolysis 14. This water separated off in the distillation can optionally also firstly be treated, for example to remove methanol by means of a membrane process. Substances dissolved in the water or other impurities can optionally be separated off by suitable methods. If no treatment of the water separated off in the distillation is necessary, the reaction can be carried out without wastewater being formed in this variant of the process. If treatment of the water is necessary, the wastewater from the treatment 16 is discharged from the system via the wastewater conduit 42.

Figure 3:
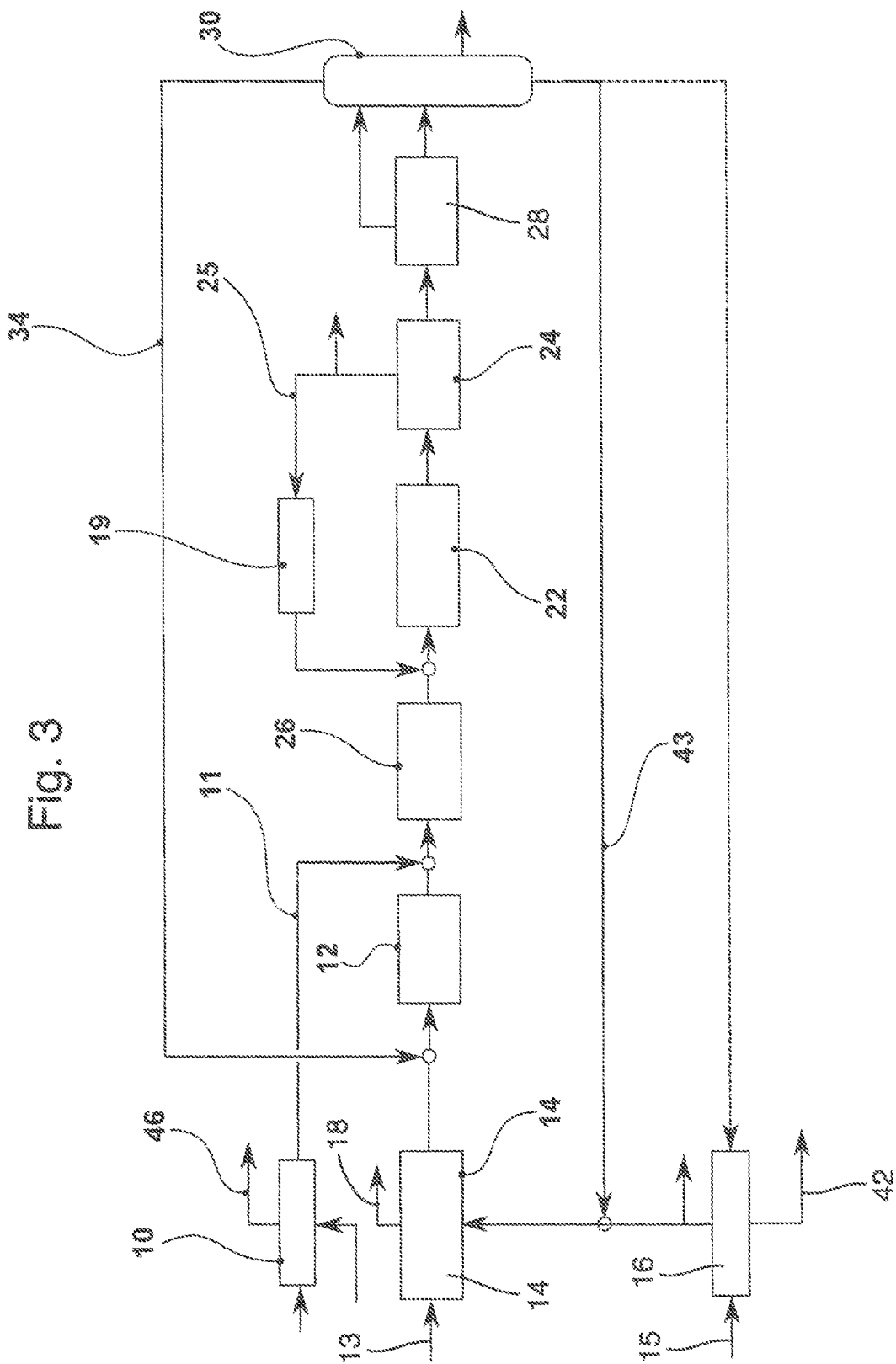
FIG. 3 is a schematic flow diagram of a third example plant for preparation of methanol.

A further difference in the variant as shown in FIG. 3 is that cooling medium from a closed cooling circuit 46 is used to vaporize the cryogenic $CO_2$ in the vaporizer 10 and heat it before it is conveyed via the conduit 11 to the second compressor stage 26. A glycol/water mixture can be used as coolant. The heated cooling medium thus does not have to be cooled separately but instead the heat present in the cooling medium can be utilized for the vaporization of $CO_2$.

A fourth embodiment of the present invention is explained below with reference to FIG. 4. This plant concept for the methanol synthesis corresponds essentially to that described above with reference to FIG. 3, with the difference than in the variant as per FIG. 4 an offgas stream is provided and is discharged from the system. From the return conduit 34, which recirculates the recycle stream from the top of the distillation apparatus 30 into the region upstream of the first compressor (or the compressor stage) 12, a substream is branched off via an offgas conduit 37 and discharged from the system. However, the amount of offgas can be minimized since, both in the variant as per FIG. 4 and in that as per FIG. 3, the gas phase from the low-pressure separator 28 is passed directly via a further conduit 45 into the distillation apparatus (distillation column) 30. The total efficiency of the plant is increased thereby. The variant as per FIG. 4 also discloses the possibility of additionally providing a small offgas stream 47 which is branched off from the conduit 25 via which the recycled gas is recirculated to the methanol synthesis. Due to the offgas stream 47, the recycled gas stream does not become too large and the ratio of $H_2$ to $CO_2$ in the reactor can be set within certain limits. A further manipulated variable for setting the desired $H_2$ to $CO_2$ ratio is the introduction of the two starter materials $CO_2$ and $H_2$ upstream of the mixing and compression section.

A fifth working example of the present invention is explained below with reference to FIG. 5. This plant concept for the methanol synthesis represents a variant in which no stream of offgas, or a minimal stream of offgas, is discharged from the system. It differs from the above-described variant as per FIG. 3 in that a substream is branched off via conduit 44, which opens into the further conduit 45, from the recycle gas which is recirculated from the high-pressure separator 24 via the return conduit 25 and the compressor 19 to the methanol synthesis 22. An alternative to this would be direct introduction into the distillation apparatus 30. In this way, this substream can be mixed into the gas stream which goes directly from the low-pressure separator 28 to the distillation apparatus 30. Taking off a substream from the recycle gas enables a constant stream to be recirculated via the recycle compressor 19 to the methanol reactor 22. The division of the stream creates flexibility in respect of the amount recirculated.

The return conduit 34 provided in the variants as per FIGS. 3 to 7 conveys the gas stream from the distillation apparatus 30 back to a point upstream of the compressor 12 by means of which the feed gas is compressed. The gas stream from the low-pressure separator 28 is fed into the distillation apparatus 30. A substream of the gas stream from the high-pressure separator 24 can, as is shown in the working examples as per FIGS. 5 to 7, likewise be fed via the conduits 44 and to the distillation apparatus 30. As an alternative, the gas stream from the high-pressure separator 24 can, however, be recirculated either in its entirety as in the variants shown in FIGS. 3 and 4 or partly as in the variants shown in FIGS. 5 to 7, optionally with compression by means of the further compressor 19, to the inlet of the methanol synthesis reactor 22. The efficiency of the methanol plant of the invention is significantly improved by these measures.

Figure 4:
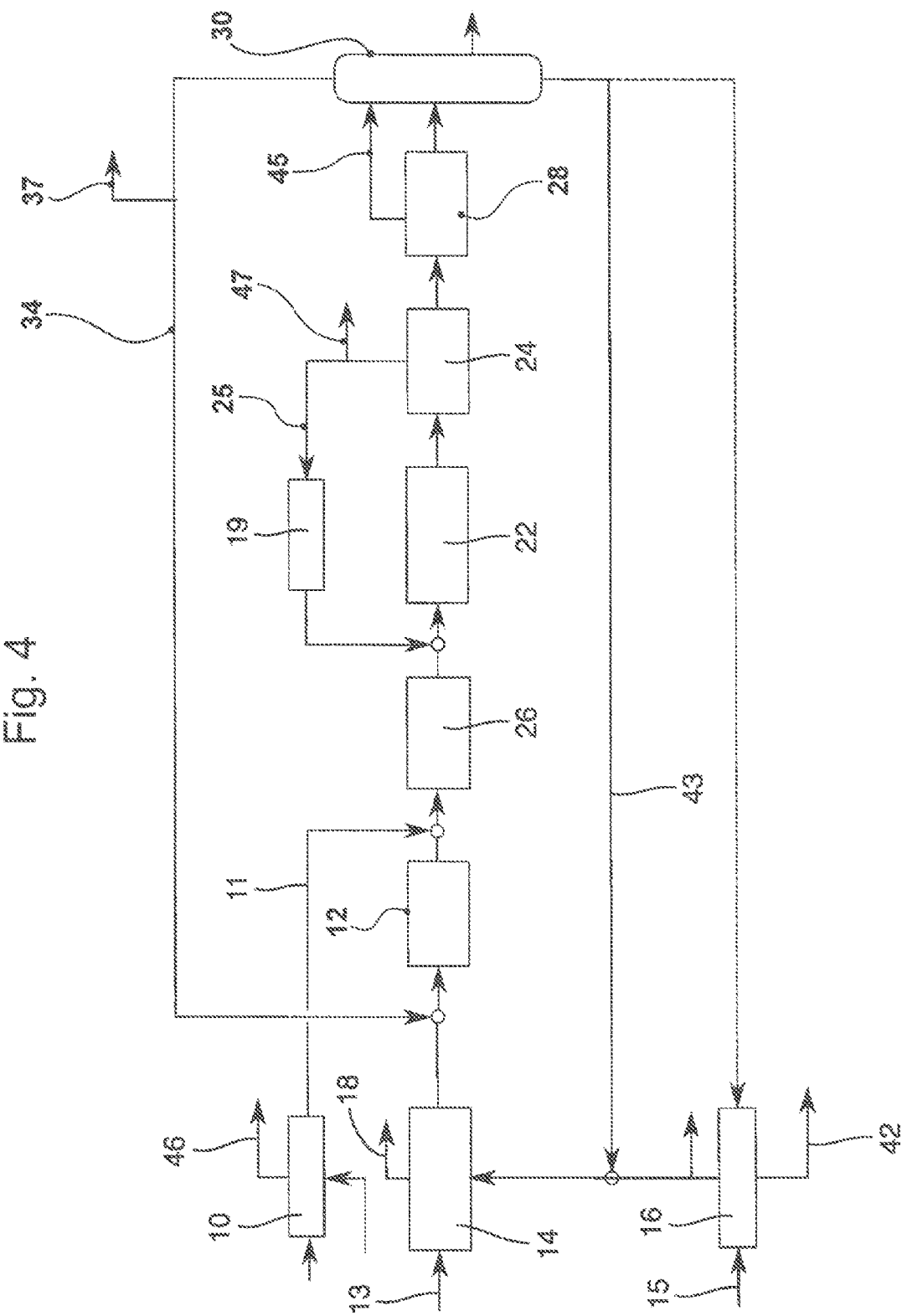
FIG. 4 is a schematic flow diagram of a fourth example plant for preparation of methanol with discharge of part of purge gases/offgases.
Figure 5:
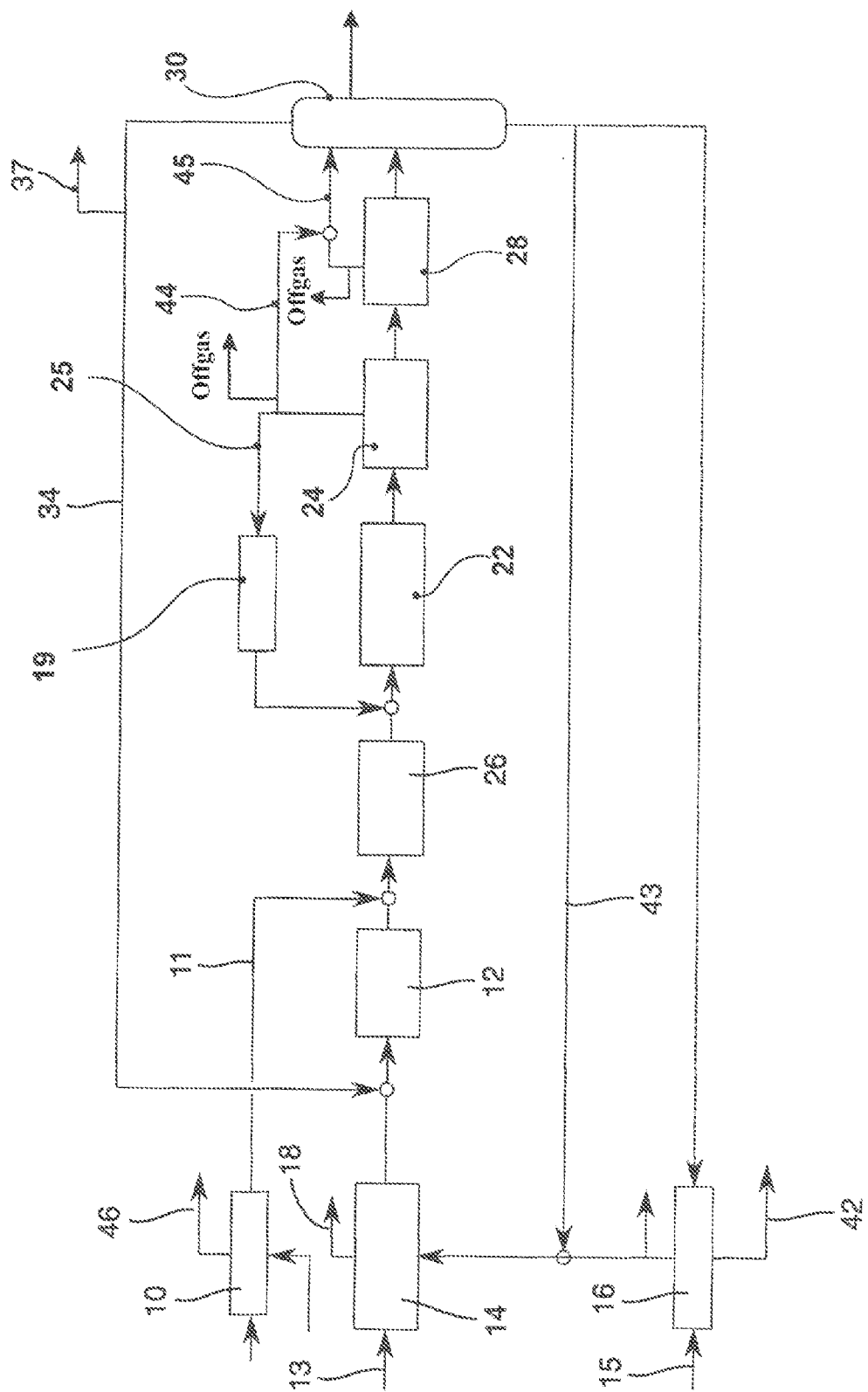
FIG. 5 is a schematic flow diagram of a fifth example plant for preparation of methanol without discharge of an offgas stream.

The integrated configuration of the methanol plant in the working examples shown in FIGS. 3 to 5 has the advantage that the amount of offgas obtained in the process can be significantly reduced. In addition, the amount of the feed gases carbon dioxide and hydrogen can be reduced considerably, for example by a few percentage points, at the same amount of methanol produced. The quantity of electric power required in the electrolysis for obtaining the hydrogen is also reduced in this way.

The vaporizer 10 for vaporizing the cryogenic carbon dioxide, as shown in the working examples as per FIGS. 2 to 6, produces cold which can, for example, be used for cooling the stream of hydrogen from the electrolysis. The stream of hydrogen can in this way be cooled down to temperatures in the region of, for example, less than 5° C. As a result, it is possible to recover a high proportion of water which can then be conveyed back into the electrolysis apparatus 14 for the water electrolysis. A glycol/water mixture, for example, serves as cooling medium here.

Furthermore, the process water obtained as coproduct in the process can advantageously be recirculated to the electrolysis apparatus 14, for example via the return conduit 43 depicted in FIG. 3.

Further advantages of the process are given by the apparatus 36 for catalytic offgas purification as described above with the aid of FIG. 2.

A sixth working example of the present invention will be explained below with reference to FIG. 6. This plant concept for the methanol synthesis provides for discharge of a small offgas stream 37 from the return conduit 34 via which the recycle stream is recirculated to the region upstream of the compressor 12. Such a small offgas stream 37 can, for example, be obtained when a catalyst having poor selectivity is used or unfavorable operating parameters are selected when deactivation of the catalyst has progressed and by-products are thus formed to an increased extent.

Figure 6:
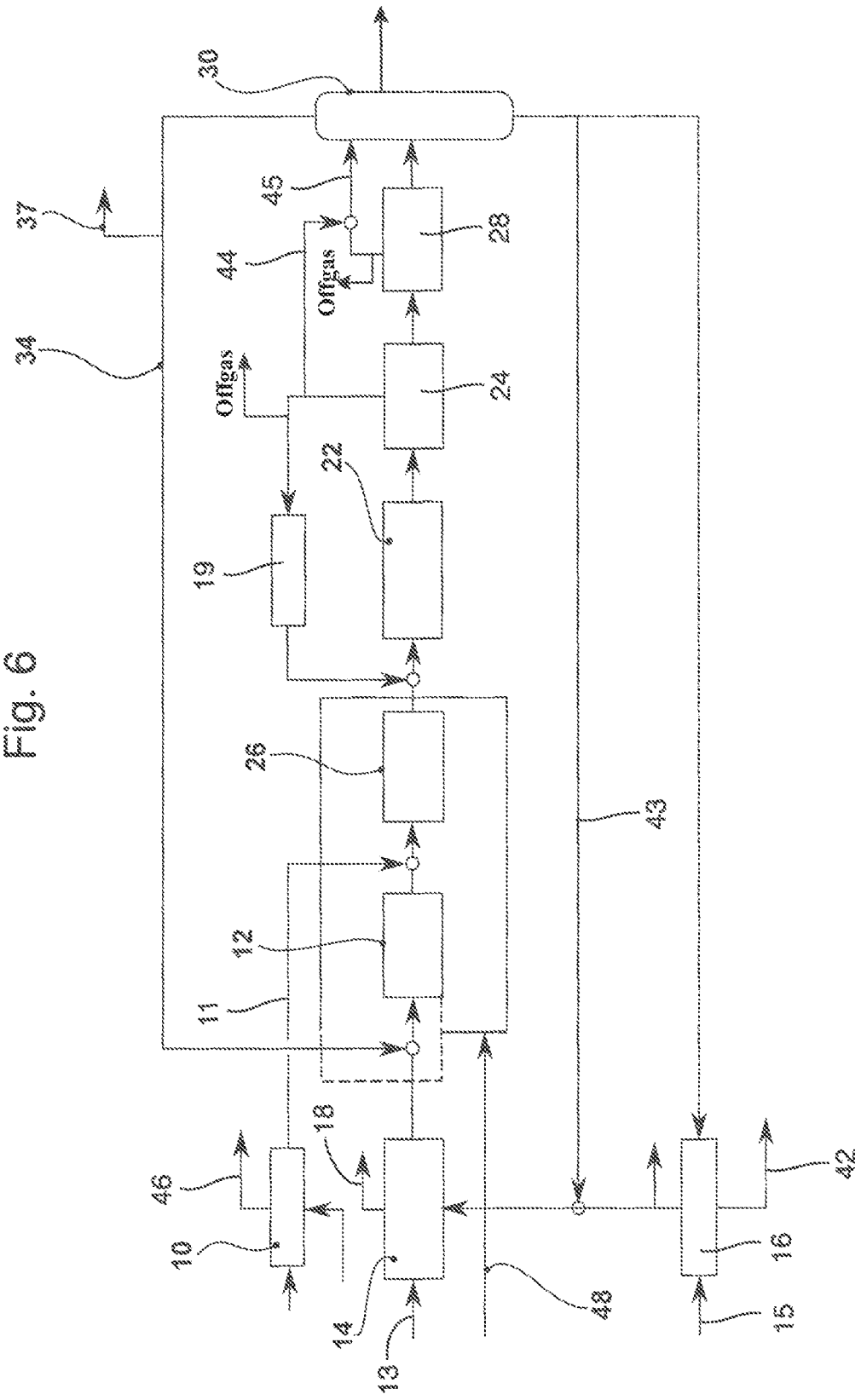
FIG. 6 is a schematic flow diagram of a sixth example plant for preparation of methanol with introduction of further feed gases into methanol synthesis.

This embodiment as per FIG. 6 also differs from the above-described variants in that further feed gases are introduced from outside the system into the mixing and compression section which comprises the two compressors 12 and 26 or compressor stages. A further conduit 48 which leads from outside to the mixing and compression section and via which CO, $H_2$ or a synthesis gas comprising CO, $CO_2$ and $H_2$ can be introduced is provided. These further gases are mixed in the mixing and compression section with the hydrogen from the electrolysis 14 and/or the carbon dioxide from the vaporizer and the mixture is then fed to the methanol synthesis reactor 22.

Figure 7:
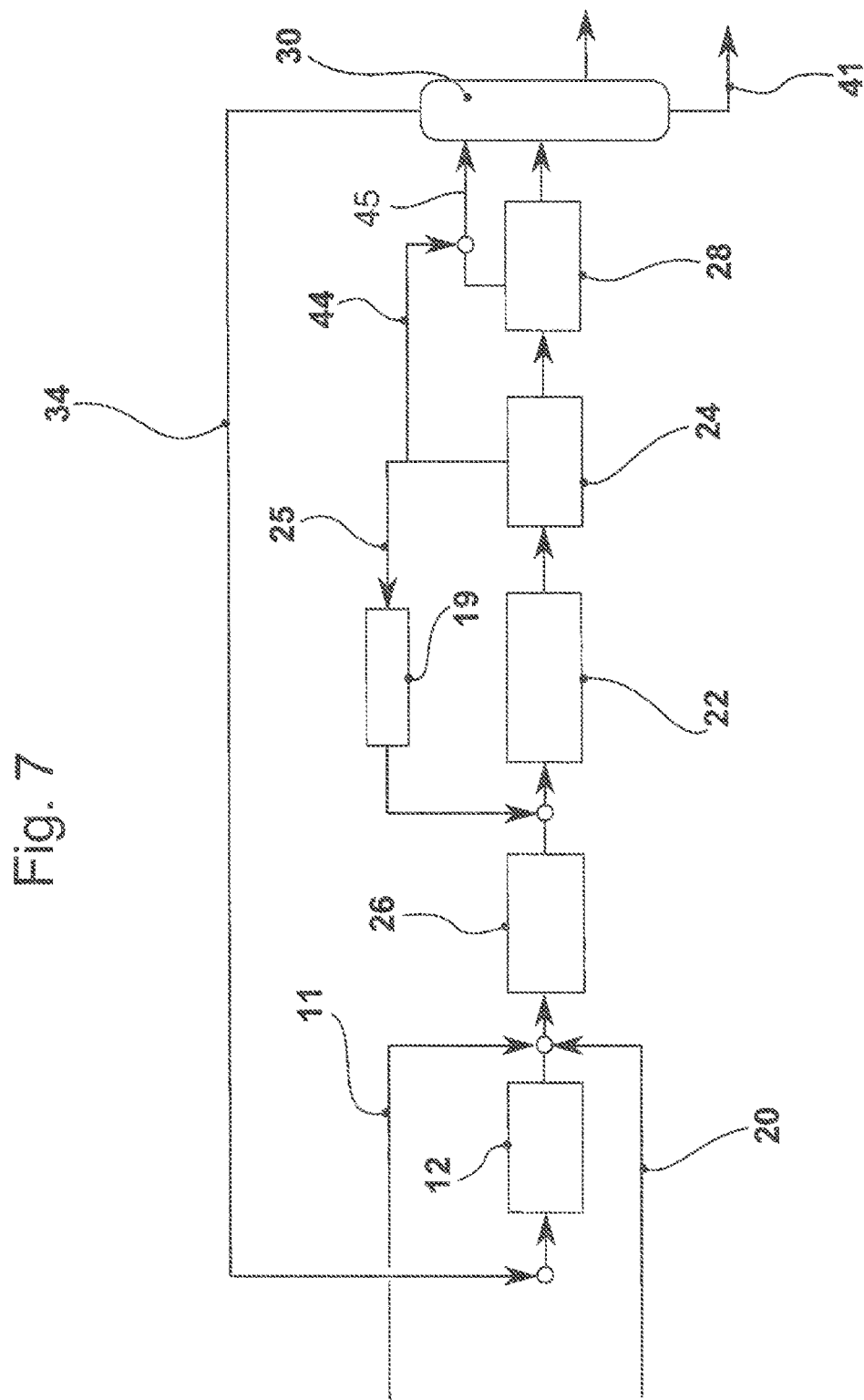
FIG. 7 is a schematic flow diagram of a seventh example plant for preparation of methanol with a simplified plant configuration.

A seventh working example of the present invention is explained below with reference to FIG. 7. This variant relates to a somewhat simplified plant concept for the synthesis of methanol. Here, carbon dioxide is fed from outside the system in the gaseous state via the conduit 11 into a region which is arranged downstream of the first compressor or the first compressor stage 12. The hydrogen is not produced in the system by electrolysis but is instead also supplied from outside via the conduit 20, which comes into consideration when, for example, hydrogen is available at a site. Any other combinations for provision of the feed gases are also possible, for example the use of $H_2$ from the electrolysis in combination with gaseous $CO_2$ or, for example, the use of $H_2$ from outside in combination with cryogenic $CO_2$. In FIG. 7, too, an offgas stream 37 can be provided in a manner analogous to that described above in the case of FIG. 6.

The two feed gases go into the region between the first compressor or the first compressor stage 12 and the second compressor or the second compressor stage 26. Here, the way in which compression is carried out is also dependent on the pressure level of the gases present. Introduction downstream of the first compressor stage represents one of several alternative possibilities. The gases can, in a manner analogous to FIG. 7, be introduced into the mixing and compression section at any point, depending on the pressure level at which the gas is present. The recycle stream recirculated from the distillation apparatus 30 via the return conduit 34 is, on the other hand, fed into a region upstream of the first compressor 12 and is there firstly compressed and then, at the outlet end of the first compressor 12, mixed with the fresh feed gases hydrogen and carbon dioxide introduced from the outside and this mixture is fed into the second compressor 26. The recycle gas is, as described above in the case of the variant of FIG. 1, conveyed from the high-pressure separator 24 via the return conduit 25 through the compressor 19, compressed there and then mixed in the region downstream of the second compressor 26 with the fluid stream produced there and fed into the methanol synthesis reactor 22.

Figure 2:
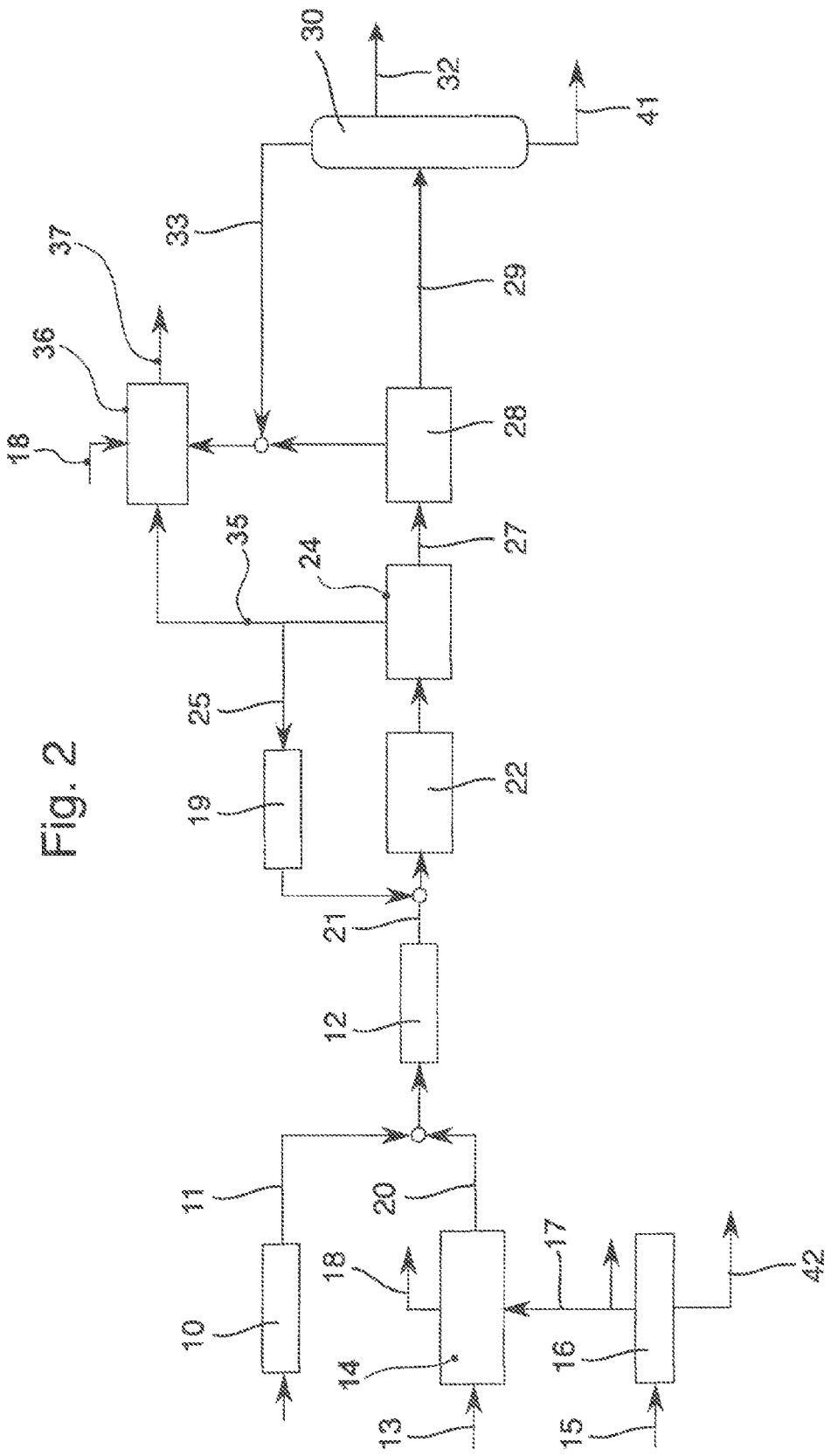
FIG. 2 is a schematic flow diagram of a second example plant for the preparation of methanol with catalytic combustion of part of purge gases/offgases.

The process water is not recycled in this variant since no production of hydrogen by electrolysis is provided in the system but instead, as in the variant in accordance with FIG. 1, the water separated off in the distillation apparatus 30 can be discharged from the system via a conduit 31 from the bottom of the column. In an alternative variant of the invention, it is also possible to provide an additional $H_2$ store in the plant, with, for example, the $H_2$ being stored under superatmospheric pressure in a vessel. For example, in a plant concept as has been described above with reference to FIG. 3, the $H_2$ store can be arranged in the region of the first compressor 12, with, for short-term equalization of relatively small fluctuations, a conduit which leads to the inlet side of the $H_2$ store being branched off downstream of the first compressor 12 and upstream of the second compressor 26 and a conduit being able to lead back from the outlet side of the $H_2$ store into the region upstream of the first compressor 12. Thus, for example, when there is low power availability, the capacity of the actual methanol plant can be adapted in a regulated manner. This is especially advantageous for the distillation column 30. Pure hydrogen is not stored by means of the branch downstream of the first compressor stage 12. However, the $H_2$ content is, for example, above 98%. Further components such as $CO_2$, CO, methanol, dimethyl ether and methyl formate get in via the recycle stream. In return, however, there is the advantage that no additional compressor is necessary.

When, for example, proton exchange membrane electrolyzers (PEM electrolyzers) are used, the $H_2$ is obtained at relatively high pressures (for example up to 35 bar) and can then be stored directly without a compressor stage.

When relatively large storage capacities for hydrogen are necessary, an alternative variant can be chosen. For example, a branched conduit for hydrogen which branches off downstream of the water electrolysis 14 and upstream of the first compressor 12 and leads firstly to a further compressor in order to bring the hydrogen to a higher pressure and store it at a higher pressure can be provided in the plant flow diagram depicted in FIG. 3. The hydrogen store from the outlet of which a conduit leads into the region between the first compressor 12 and the second compressor 26 is then arranged downstream of this further compressor (see plant flow diagram in FIG. 3). In this way, pure $H_2$ can be stored at higher pressures by means of the additional compressor. Here too, the introduction can also be effected, as an alternative, upstream of the first compressor 12.

LIST OF REFERENCE NUMERALS

10 Vaporizer
11 Conduit for $CO_2$
12 Compressor
13 Inlet conduit for stream
14 Electrolysis apparatus
15 Feed conduit for water
16 Water treatment
17 Feed conduit for water
18 Conduit for oxygen
19 Compressor
20 Conduit for hydrogen
21 Conduit for starter materials
22 Methanol synthesis reactor
23 Conduit for product
24 High-pressure separator
25 Return conduit (recycle gas conduit)
26 Compressor
27 Conduit
28 Low-pressure separator
29 Conduit
30 Distillation apparatus
31 Second conduit
32 Outlet conduit for methanol
33 Conduit
34 Return conduit
35 Conduit to after-combustion
36 Apparatus for catalytic offgas purification
37 Outlet conduit
38 Crude methanol tank
39 Flare
40 Offgas conduit
41 Wastewater conduit
42 Wastewater conduit
43 Return conduit for process water
44 Conduit for substream
45 Conduit
46 Coolant circuit
47 Offgas stream
48 Further conduit to mixing and compression section

What is claimed is:

1. A process for preparing methanol comprising:
feeding a methanol containing product stream obtained from a methanol synthesis reaction that reacts carbon dioxide with hydrogen to a high-pressure separator and a low-pressure separator where gas streams containing volatile components are respectively separated off from the methanol-containing product stream;
feeding the methanol-containing product stream, after the gas streams are separated off, to a distillation step where a gas stream containing volatile components and water are separated off from the methanol-containing product stream;
feeding the gas stream that has been separated off in the low-pressure separator to the distillation step; and
recirculating the gas stream containing volatile components that has been separated off in the distillation step at least partly into a mixing and compression section located upstream of a reactor that conducts the methanol synthesis reaction.

2. The process of claim 1 comprising at least one of
at least partially discharging the gas streams containing volatile components as offgas, or
recirculating at least part of the gas streams containing volatile components to the methanol synthesis reaction.

3. The process of claim 1 comprising feeding at least one substream of the gas streams to a catalytic offgas purification.

4. The process of claim 3 wherein the catalytic offgas purification comprises a catalytic after-combustion with introduction of a supplementary combustion component.

5. The process of claim 4 wherein oxygen obtained by electrolysis is introduced as the supplementary combustion component.

6. The process of claim 1 comprising obtaining the hydrogen used as a starter material in the methanol synthesis reaction by electrolysis of water.

7. The process of claim 6 wherein the water that has been separated off from the methanol-containing product stream in the distillation step is at least partially recirculated for the electrolysis.

8. The process of claim 6 comprising treating the water that is used as a starter material for the electrolysis by at least one of ion exchange or reverse osmosis.

9. The process of claim 6, further comprising feeding the methanol-containing product stream, after the gas streams are respectively separated off in the high-pressure separator and the low pressure separator, to a condensation step where water is separated off from the methanol-containing product stream; and at least partially recirculating the water that has been separated off by the condensation step for the electrolysis.

10. The process of claim 1 wherein liquid carbon dioxide is used as a starter material for the carbon dioxide reacted in the methanol synthesis reaction.

11. The process of claim 10 comprising vaporizing and heating the liquid carbon dioxide with heat from a return stream of a cooling medium used by the process.

12. The process of claim 1 wherein the mixing and compression section includes one or more compressors or compressor stages connected in series.

13. The process of claim 1 comprising discharging a substream of the gas stream containing volatile components separated off in the distillation step as offgas.

14. The process of claim 1 comprising supplying the mixing and compression section with carbon monoxide or hydrogen or a synthesis gas containing carbon oxides and hydrogen from outside a plant where the process occurs.

15. The process of claim 1 comprising:
recirculating water that has been separated off in the distillation step as process water for electrolytic production of hydrogen.

16. The process of claim 1 comprising:
compressing the recirculated gas stream that has been separated off in the distillation step in a first compressor or a first compressor stage of the mixing and compression section, which generates a compressed recirculated stream;
combining at least one of the carbon dioxide or the hydrogen as feed gases with the compressed recirculated stream, which generates a resulting combined mixture;
feeding the resulting combined mixture to a second compressor or a second compressor stage; and
feeding the resulting combined mixture, after the second compressor or the second compressor stage, to the methanol synthesis reaction.

17. A process for preparing methanol comprising:
feeding a methanol-containing product stream obtained from a methanol synthesis reaction that reacts carbon dioxide with hydrogen to a pressure separator where a gas stream containing volatile components is separated off from the methanol-containing product stream;
feeding the methanol-containing product stream, after the gas stream is separated off, to a distillation step where a gas stream containing volatile components and water are separated off from the methanol-containing product stream;
recirculating the gas stream containing volatile components that has been separated off in the distillation step at least partly into a mixing and compression section located upstream of a reactor that conducts the methanol synthesis reaction;
at least partially recirculating the gas stream that has been separated off in the pressure separator as recycle gas to the methanol synthesis reaction; and
feeding a substream of the gas stream that has been separated off in the pressure separator to the distillation step.

18. A process for preparing methanol comprising:
feeding a methanol-containing product stream obtained from a methanol synthesis reaction that reacts carbon dioxide with hydrogen to a high-pressure separator and a low-pressure separator where a first gas stream containing volatile components is separated off from the methanol-containing product stream in the high pressure separator and a second gas stream containing volatile components is separated off from the methanol containing product stream in the low-pressure separator;
feeding the methanol-containing product stream, after the first gas stream and the second gas stream are separated off, to a distillation step where a gas stream containing volatile components and water are separated off from the methanol-containing product stream;
recirculating the gas stream containing volatile components that has been separated off in the distillation step at least partly into a mixing and compression section located upstream of a reactor that conducts the methanol synthesis reaction;
at least partially recirculating the first gas stream as recycle gas to the methanol synthesis reaction; and
feeding the second gas stream to the distillation step.

* * * * *